US00PP24656P3

(12) United States Plant Patent
Coiner

(10) Patent No.: US PP24,656 P3
(45) Date of Patent: Jul. 22, 2014

(54) HYBRID TEA ROSE PLANT NAMED 'J.C.'S PRIDE'

(50) Latin Name: *Rosa hybrida*
Varietal Denomination: J.C.'s Pride

(76) Inventor: James W. Coiner, Covina, CA (US)

( * ) Notice: Subject to any disclaimer, the term of this patent is extended or adjusted under 35 U.S.C. 154(b) by 95 days.

(21) Appl. No.: 13/573,322

(22) Filed: Sep. 11, 2012

(65) Prior Publication Data

US 2014/0075608 P1 Mar. 13, 2014

(51) Int. Cl.
*A01H 5/00* (2006.01)

(52) U.S. Cl.
USPC ..... Plt./138; Plt./130; Plt./139

(58) Field of Classification Search
USPC ..... Plt./130, 138, 139
See application file for complete search history.

*Primary Examiner* — Susan McCormick Ewoldt
(74) *Attorney, Agent, or Firm* — Christie, Parker & Hale, LLP

(57) ABSTRACT

A new variety of Hybrid Tea rose suitable for garden decoration, having flowers of red coloration.

1 Drawing Sheet

Classification:

The present invention relates to a new *Rosa hybrida* plant.

Variety denomination: The new plant has the varietal denomination 'J.C.'S PRIDE'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant is a dwarf-like bushy trailing compact upright growing spreading climbing sprawling plant growth habit, suitable for outdoor garden decoration.

Asexual reproduction of the new variety by budding as performed in Kern County shows that the foregoing and other distinguishing characteristics come true to form and are established and transmitted through succeeding asexual propagations. 'J.C's Pride' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Melody Parfumee' (U.S. Plant Pat. No. 11,014) by the following combination of characteristics: a deeper coloration, on a very strong neck with shiny foliage.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly, sometimes usually in clusters of two to three or more per stem. Flowers may be borne in regular flat to rounded clusters having strong long stems (about 45 cm to about 120 cm). Outdoors, the plant blooms abundantly and nearly continuously during the growing season. The flowers have a slight tea fragrance.

BUD

The peduncle is about 5 cm to about 8 cm in length, average caliper (about 3 mm to about 5 mm in diameter), and usually erect. It is usually smooth, with many stipitate glands, and some hairs and prickles. Peduncle color is near between 140a and 140b.

Before the calyx breaks, the bud is about 1.8 cm to about 1.2 cm in diameter at the widest point, about 3 cm to about 3.9 cm in length, and ovoid in shape with a conspicuous neck. The surface of the bud bears some foliaceous appendages moss tomentum stipitate glands and glandular bloom, usually with slender entire bristle-like foliaceous parts extending beyond the tip of the bud about one half or more of its length. Bud color is near between 144a and 147c.

The sepals are about 3 cm to about 4 cm in length and about 1 cm to about 2 cm in width at the widest point. The outer surface color of the sepal is near between 144A and 147C. The inner surface color of the sepal is near between 143C and 139C and covered edges with fine wooly tomentum; sepal margins are lined with few stipitate glands and hairs.

The receptacle of the flower is of somewhat long in length (about 1.2 cm to about 8 cm). The receptacle is funnel shaped in form. Its surface is smooth. The receptacle color is near between 140a and 140b.

As the petals open (after the calyx breaks), the bud is about 2.2 cm to about 3.3 cm in diameter at the widest point, about 3.3 cm to about 4.6 cm in length, and ovoid in form. The color of the upper sides of the petal are near 64a to 64b, on the inner half and blending to near 74a and 74b at the apex. The reverse sides of the petal are near 66b at the base, and near 74b on the edges.

BLOOM

When fully open, the bloom ranges from about 12 cm to about 13 cm in diameter. Petalage is double with about 35 to 40 petals and no petaloids. When partially open, the bloom form is somewhat cupped to high centered, and the petals are somewhat tightly spiraled to imbricated with petal edges somewhat rolled outward. When fully open, the bloom form is somewhat full to globular, and the petals are impricated with petal edges moderately rolled outward.

PETALS

The substance of the petal is somewhat heavy to leathery and of medium thickness, with upper surfaces somewhat velvety and the under surfaces velvety, with notched apexes.

The outer petals are somewhat round to ovate in shape with notched apexes. The petals are about 4.4 cm to 5 cm in length and 4 cm to 5.6 cm in width at the widest point.

NEWLY OPENED FLOWER

The upper surface color of the outer petals is near between 74a and 74b.

The upper surface color of the intermediate petals is near between 64b and 64c.

The upper surface color of the inner petals is near between 64a and 64b.

The general tonality of the newly opened flower is near 74b.

THREE-DAY OLD FLOWER

Upper surface color of the outer petals is near between 74a and 74b.

The upper surface color of the intermediate petals is near between 64b and 64c.

The upper surface color of the inner petals is near between 64a and 64b.

The general tonality of the newly opened flower is near 74b.

On the spent bloom, the petals usually drop off cleanly, fading to near between 64c and 64d.

In October in Wasco, Calif., blooms on the bush growing outdoors generally last about 6 to 7 days. Cut flowers indoors generally last 4 to 5 days.

MALE REPRODUCTIVE ORGANS

Stamen are average in number usually about 110, and arranged regularly around the pistils. The filaments are of irregular lengths, most with anthers. The anthers are somewhat small for the class and all open at about the same time. Anther color is near 17a when immature and near 165c at maturity. Pollen is moderate and near 21c in color.

FEMALE REPRODUCTIVE ORGANS

The Pistils vary in number (average about 80). The styles are somewhat uneven, somewhat loosely bunched. Style color is near between 9 and 9c. Ovaries are all enclosed in the calyx.

Hips have not been observed on this variety when grown in Wasco, Calif.

FOLIAGE

The compound leaves are usually comprised of three to five leaflets and are borne abundantly in normal quantities. The five-leaflet leaves are about 14 cm to about 18 cm in length and about 13.5 cm to about 16 cm in width at the widest point, somewhat leathery to crisp in texture, and moderately glossy to semi-glossy in finish. The terminal leaflets are about 6.5 cm to about 10.5 cm in length and about 4.5 cm to about 6.0 cm in width at the widest point and are shaped ovate.

The upper surface color of the mature leaf is near between 141b and 141c. The under surface color of the mature leaf is near between 138b and 138c. The upper surface color of the young leaf is near between 141c and 141d. The under surface color of the young leaf is near between 138c and 138d.

The rachis is somewhat light in caliper and moderately smooth. The upper side is shallowly grooved with few hairs and stipitate glands and prickles on the edges of the grooves. The under side of the rachis is smooth with few hairs and stipitate glands and moderately small to medium to large prickles. The rachis color is near between 144c and 146d.

The stipules are about 1.2 cm to about 1.6 cm in length and very moderately wide (about 4 mm to about 7 mm) with moderately short to medium points that usually sometime turn out at an angle of more than 90 degrees curved toward the stem. The stipules color is near between 144c and 144d.

The petiole is somewhat light in caliper and somewhat smooth. The upper side is shallowly grooved with some hairs and stipitate glands and prickles on the edges of the grooves. The petiole is about 1 cm to about 2 cm in length and about 2 mm to about 3 mm in diameter at the widest point. The petiole color is near between 144c and 146d.

The plant displays an average to above-average degree of resistance to powdery mildew and rust as compared to other commercial varieties grown under comparable conditions in Wasco, Calif. The plant's winter hardiness and drought/heat tolerance are yet to be determined.

GROWTH

The plant has an upright to tall growth habit (about 150 cm to about 160 cm in height and about 80 cm to about 80 cm spread at the widest point), with full branching. It displays vigorous growth and the canes are of medium to heavy caliper for the class.

The color of the major stems is near between 144a and 138b. They bear few large prickles that are about 10 mm to about 8 mm in length. The large prickles are hooked slightly downward with a somewhat medium length to rounded base; prickle color is near between 138d and 139d.

The color of the branches is near between 136c and 136d. They bear prickles which are of similar size and shape to the large prickles on the major stems; prickle color is near between 138c and 138d.

The color of the new shoots is near between 136c and 136d. They bear prickles; prickle color is near between 164c and 164d. The shoots bear prickles of similar shape and coloration and which are near between 160c.

I claim:

1. A new and distinct Hybrid Tea rose plant of the variety substantially as described and illustrated herein.

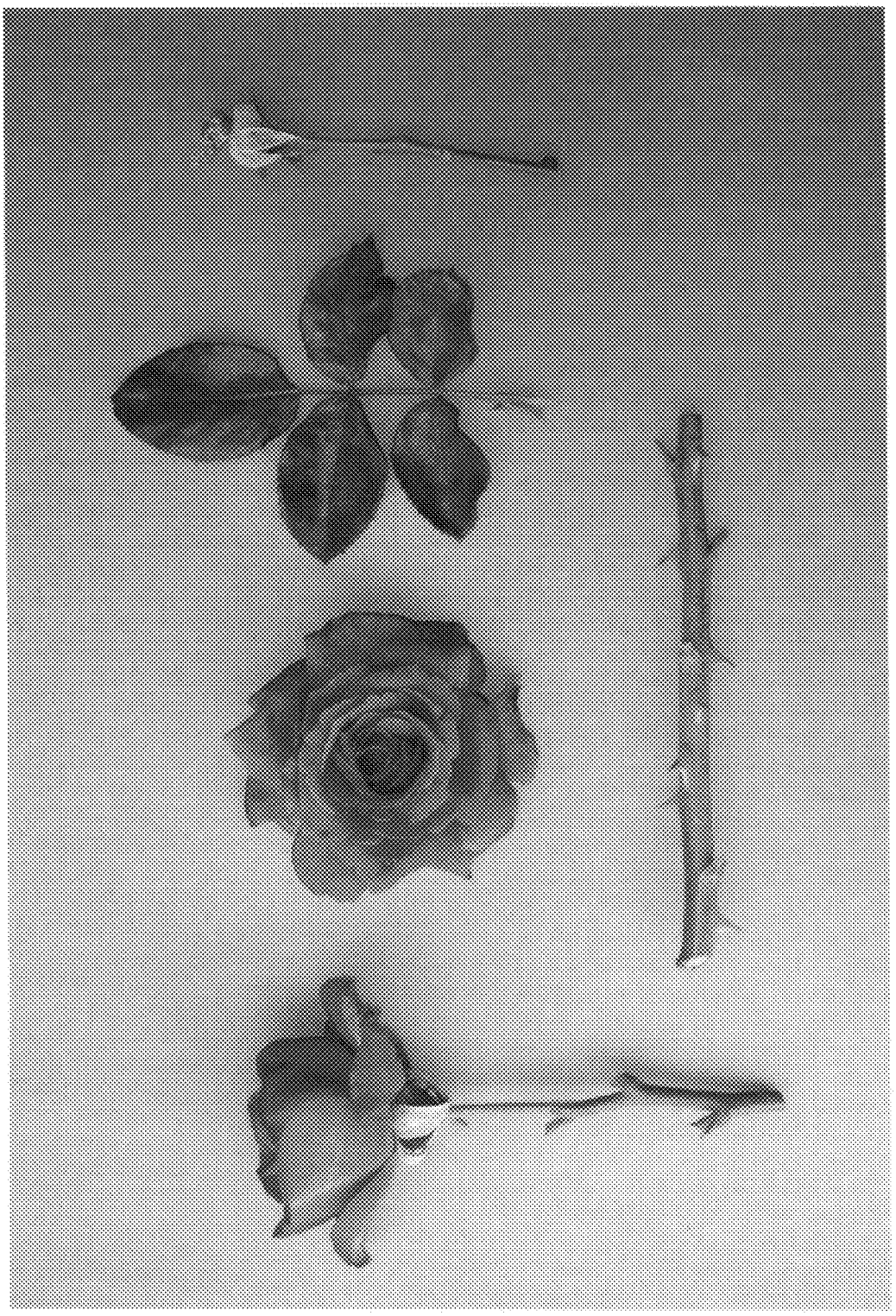

* * * * *